(12) United States Patent
Doyle (10) Patent No.: US 7,881,510 B2
(45) Date of Patent: Feb. 1, 2011

(54) METHOD AND APPARATUS FOR FORMING AN IMAGE WITH DYNAMIC PROJECTIVE DATA

(75) Inventor: Mark Doyle, Wexford, PA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 907 days.

(21) Appl. No.: 11/811,082

(22) Filed: Jun. 8, 2007

(65) Prior Publication Data

US 2008/0304727 A1 Dec. 11, 2008

(51) Int. Cl.
G06K 9/00 (2006.01)
(52) U.S. Cl. .................. 382/128; 382/130; 382/131; 382/132
(58) Field of Classification Search .......... 382/128, 382/130, 131, 132
See application file for complete search history.

(56) References Cited

U.S. PATENT DOCUMENTS

2005/0251023 A1* 11/2005 Kannengiesser et al. .... 600/410
2007/0242866 A1* 10/2007 Schmitt et al. .............. 382/130

\* cited by examiner

Primary Examiner—Tom Y Lu
(74) Attorney, Agent, or Firm—Pepper Hamilton LLP (57) ABSTRACT

An apparatus for forming an image of a body of a patient. The apparatus comprises an energy source which emits energy that passes through the body or which causes the body to emit energy. The apparatus comprises at least one detector element which receives the energy which has pass through, or originated within the body. The apparatus comprises a computer with a memory in communication with the detector element which stores in the memory angular and timing information relative to the body regarding the energy. The apparatus comprises means for obtaining additional angular and timing information relative to the body regarding the information including the computer-generated steps from a computable readable medium of: acquiring time resolved projective data, either in a sparse manner or in a highly sampled manner, depending on which acquisition aspect of the patient is to be reduced; interpolating either along a circumferential direction or along a temporal direction sparsely sampled data, the interpolation direction being determined by a relative k-space sampling density; applying data filtering either along the circumferential direction or along the temporal direction for highly sampled data, the filtering direction being determined by the relative k-space sampling density; compiling a full radial sampling set from the filtered or interpolated data; and submitting the sampling set for reconstruction. A method for forming an image of a patient.

16 Claims, 8 Drawing Sheets

CIRCUMFERENTIAL POSITION ⟶

METHOD AND APPARATUS FOR FORMING AN IMAGE WITH DYNAMIC PROJECTIVE DATA

FIELD OF THE INVENTION

The present invention is related to forming an image with dynamic projective data. More specifically, the present invention is related to forming an image with dynamic projective data where interpolation or filtering is applied circumferentially or temporally based on the density of sampling of k-space.

BACKGROUND OF THE INVENTION

The projective spatial encoding techniques are widely used in medical imaging, including nuclear medicine, computed tomography (CT), and to a lesser extent, in magnetic resonance imaging (MRI). When applied to the heart, images are acquired in a time resolved manner, typically to show motion throughout the cardiac cycle. Each image frame is reconstructed from a series of projective views of the patient, with the series of projective views for that slice at that point in the cardiac cycle taken at a number of equally spaced angular positions around the body. In CT and MRI there may be 200-300 projective views per slice per time point in the cardiac cycle, and in lower-resolution nuclear medicine, there are typically 60-100 projective views per slice per time point. To acquire projective views at multiple angles at each slice and at multiple time points throughout the cardiac cycle requires that thousands of projective views per slice are required. This requirement has different implications for each imaging modality: for nuclear medicine, long scan times result, which ultimately becomes the limiting factor; for CT imaging, each projective view requires application of an x-ray source, and radiation exposure is typically the limiting factor; in MRI, scan time is typically the limiting factor. The current invention, STAR, allows time resolved image series to be generated from a reduced set of projective data, which has different implications for each imaging modality: nuclear medicine could produce images faster and with higher resolution, CT could produce images with less radiation exposure to the patient, and MRI could produce images faster.

There is an approach that uses VIPRE, which primarily works with projective data that changes in intensity with time (such as angiographic data) but which is otherwise stationary. STAR works with dynamic projective data, but there is no requirement for the data to be stationary.

BRIEF SUMMARY OF THE INVENTION

The present invention pertains to an apparatus for forming an image of a body of a patient. The apparatus comprises an energy source which emits energy that passes through the body or which causes the body to emit energy. The apparatus comprises at least one detector element which receives the energy which has passed through, or originated within the body. The apparatus comprises a computer with a memory in communication with the detector element which stores in the memory angular and timing information relative to the body regarding the energy. The apparatus comprises means for obtaining additional angular and timing information relative to the body regarding the information including the computer-generated steps from a computable readable medium of: acquiring time resolved projective data, either in a sparse manner or in a highly sampled manner, depending on which acquisition aspect of the patient is to be reduced; interpolating either along a circumferential direction or along a temporal direction sparsely sampled data, the interpolation direction being determined by a relative k-space sampling density; applying data filtering either along the circumferential direction or along the temporal direction for highly sampled data, the filtering direction being determined by the relative k-space sampling density; compiling a full radial sampling set from the filtered or interpolated data; and submitting the sampling set for reconstruction.

The present invention pertains to a method for forming an image of a patient. The method comprises the steps of acquiring time resolved projective data, either in a sparse manner or in a highly sampled manner, depending on which acquisition aspect of the patient is to be reduced. There is the step of interpolating either along a circumferential direction or along a temporal direction sparsely sampled data, the interpolation direction being determined by a relative K-density. There is the step of applying data filtering either along the circumferential direction or along the temporal direction for highly sampled data. The filtering direction being determined by the relative k-space sampling density. There is the step of compiling a full radial sampling set from the filtered or interpolated data. There is the step of submitting the sampling set for reconstruction.

BRIEF DESCRIPTION OF THE SEVERAL VIEWS OF THE DRAWING

In the accompanying drawings, the preferred embodiment of the invention and preferred methods of practicing the invention are illustrated in which.

DETAILED DESCRIPTION OF THE INVENTION

Figure 13:
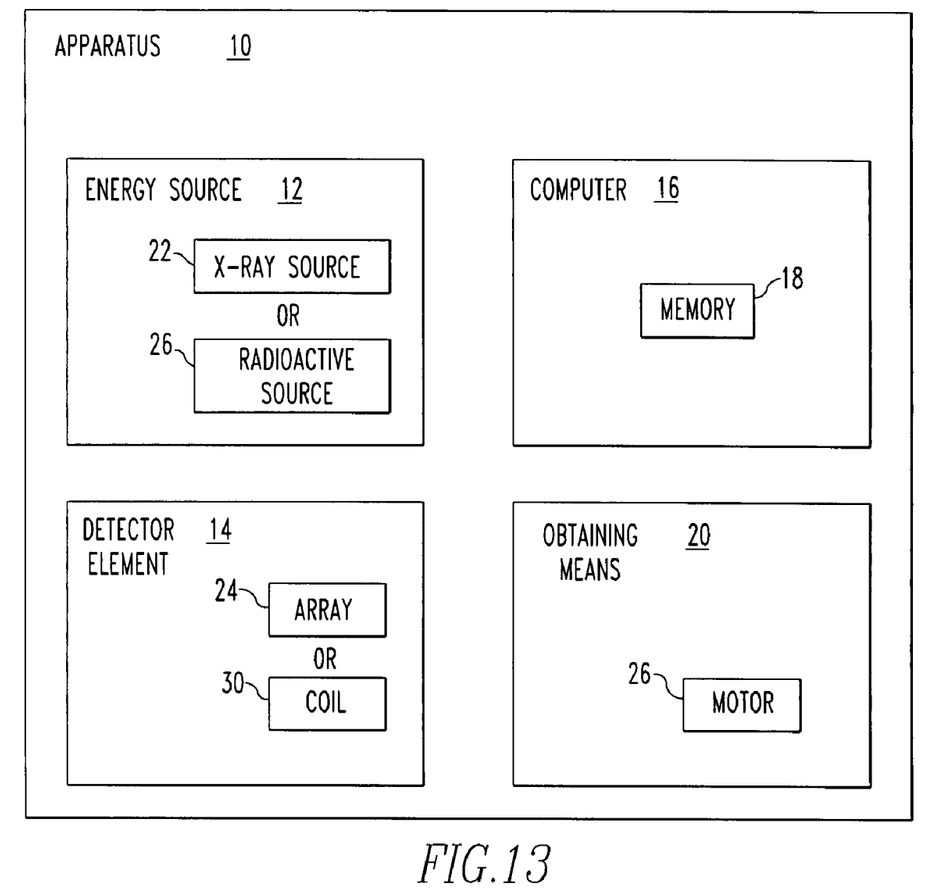
FIG. 13 is a block diagram of the apparatus of the present invention.

Referring now to the drawings wherein like reference numerals refer to similar or identical parts throughout the several views, and more specifically to FIG. 13 thereof, there is shown an apparatus 10 for forming an image of a body of a patient. The apparatus 10 comprises an energy source 12 which emits energy that passes through the body or which causes the body to emit energy. The apparatus 10 comprises at least one detector element 14 which receives the energy which has passed through, or originated within the body. The apparatus 10 comprises a computer 16 with a memory 18 in communication with the detector element 14 which stores in the memory 18 angular and timing information relative to the body regarding the energy. The apparatus 10 comprises means 20 for obtaining additional angular and timing information relative to the body regarding the information including the computer-generated steps from a computable readable medium of: acquiring time resolved projective data, either in a sparse manner or in a highly sampled manner, depending on which acquisition aspect of the patient is to be reduced; interpolating either along a circumferential direction or along a temporal direction sparsely sampled data, the interpolation direction being determined by a relative k-space sampling density; applying data filtering either along the circumferential direction or along the temporal direction for highly sampled data, the filtering direction being determined by the relative k-space sampling density; compiling a full radial sampling set from the filtered or interpolated data; and submitting the sampling set for reconstruction.

The source can be a collimated x-ray source 22. The detector element 14 can include a detector array 24. The obtaining means 20 can include a motor 26 or electrical control which moves the x-ray source 22.

The energy source 12 can include a radioactive source 28 which is adapted to be introduced to the body and which emits high-energy photons as a result of radioactive decay. The detector element 14 can include a detector array 24. The obtaining means 20 can include a motor 26 which moves the detector array 24 along a circular or a ellipsoidal trajectory around the body and when a next angular position is reached, a motor 26 stops moving the detector array 24 and the detector array 24 collects new data and position information.

The energy source 12 can produce imaging gradients that are applied in a radial manner to obtain k-space data. The detector element 14 includes a detector coil 30 and electronics which converts electrical voltage information into digital values. The obtaining means 20 includes altering the imaging gradients strengths to obtain data and a next angular position.

The present invention pertains to a method for forming an image of a patient. The method comprises the steps of acquiring time resolved projective data, either in a sparse manner or in a highly sampled manner, depending on which acquisition aspect of the patient is to be reduced. There is the step of interpolating either along a circumferential direction or along a temporal direction sparsely sampled data, the interpolation direction being determined by a relative k-space sampling density. There is the step of applying data filtering either along the circumferential direction or along the temporal direction for highly sampled data. The filtering direction being determined by the relative k-space sampling density. There is the step of compiling a full radial sampling set from the filtered or interpolated data. There is the step of submitting the sampling set for reconstruction.

Preferably, there is the step of reconstructing the sampling set to form the image. There is preferably the step of emitting energy that passes through the body. Preferably, there is the step of receiving the energy which has pass through the body with at least one detector element 14. There is preferably the step of storing in a memory 18 of a computer 16 in communication with the detector element 14 angular and timing information relative to the body regarding the energy. Preferably, there is the step of obtaining additional angular and timing information relative to the body regarding the information.

In the operation of the invention, the apparatus, otherwise known as STAR, describes a rapid acquisition and reconstruction process that is applicable to imaging approaches that acquire projective data in a time-resolved manner. The invention allows fewer projections, e.g. 75% fewer projections, compared to a full scan satisfying the Nyquist sampling criteria. The STAR scan retains spatial and temporal resolution and signal to noise ratio comparable to the fully sampled conventional scan.

The principle of the STAR invention is that projective data populate the signal space, k-space, at densities that vary along the radial axis, and that in a time resolved data set, the data at some regions of k-space are more highly sampled spatially, and at other regions of k-space the data are more highly sampled temporally. The processing applied in STAR allows two modes of operation: 1) time resolved projective data are acquired in a sparse manner and the STAR data processing applied to generate projective views that were not directly sampled, 2) time resolved projective data are acquired in a highly resolved manner, and the STAR data processing applied to generate projective views with increased signal to noise ratio. To illustrate how STAR achieves this without sacrificing spatial or temporal resolution, while preserving SNR, consider representing the projective data in the k-space format. This format is natural for most MRI acquisitions and one that is straightforwardly arranged for projective data (such as multi-detector computer tomography, MD-CT, gated-Single Photon Emission Computed Tomography, gated-SPECT). Projective data are converted to the k-space format by performing a Fourier Transform operation on projective data and arranging it in a radial pattern, See FIGS. 1A and 1B. In the radial plot of FIG. 1B, projective data lines intersect the center of k-space, with the angle of the line being in direct spatial relationship to the angle of the projective view. In the k-space representation of projective data, it is apparent that if Nyquist criteria are met at the outermost region of sampled k-space, then since the density of k-space sampling increases towards the center, this necessarily means that k-space is relatively over sampled towards the center. In contrast, the parallel line approach of sampling k-space has a uniform sampling density throughout. A representative plot of the relative density of radial vs. parallel sampling schemes as a function of radial position is shown in FIG. 2. The exact nature and degree of relative performances of the two approaches is governed by how many additional lines are acquired in a radial scan, and is given by the over sampling factor, with values of 2 to 4 being typical. In this respect, over sampling is defined as the additional number of radial lines that are acquired relative to the parallel line acquisition. In the case of an over-sampling factor of 2, the number of lines is doubled compared to a parallel scan, and yields the same Nyquist sampling density at the outermost part of k-space around the circumferential direction axes.

Figure 1A:
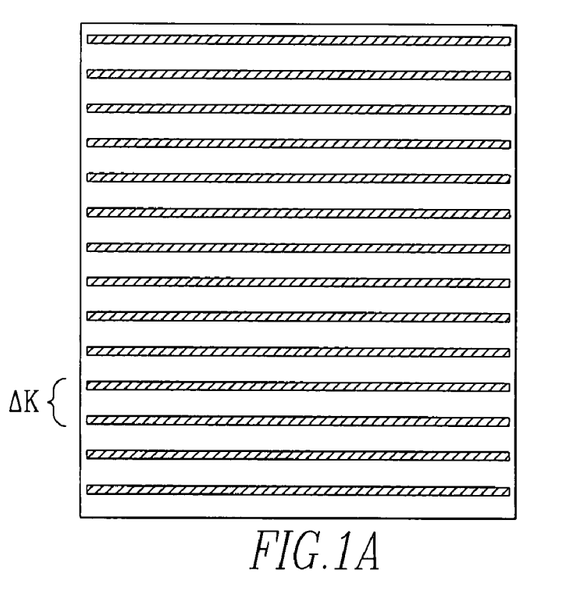
FIG. 1A shows the k-space lines arranged in a parallel manner that is typical of an MRI acquisition.
Figure 1B:
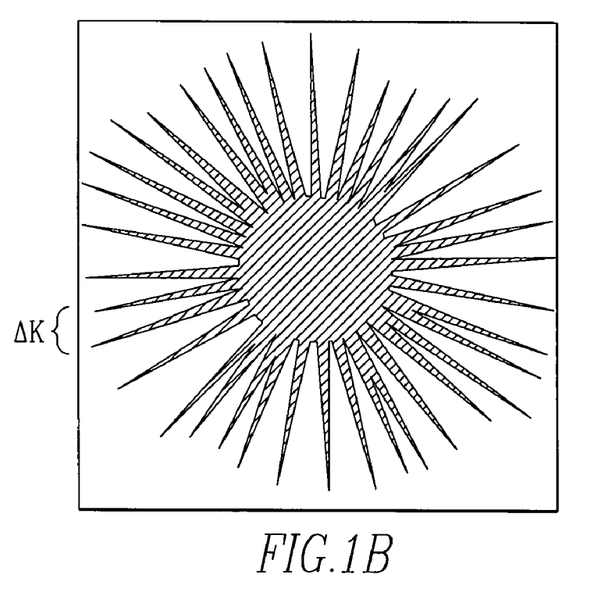
FIG. 1B corresponds to an acquisition of projective data, where each projection is represented by a separate line passing through the center of k-space.
Figure 2:
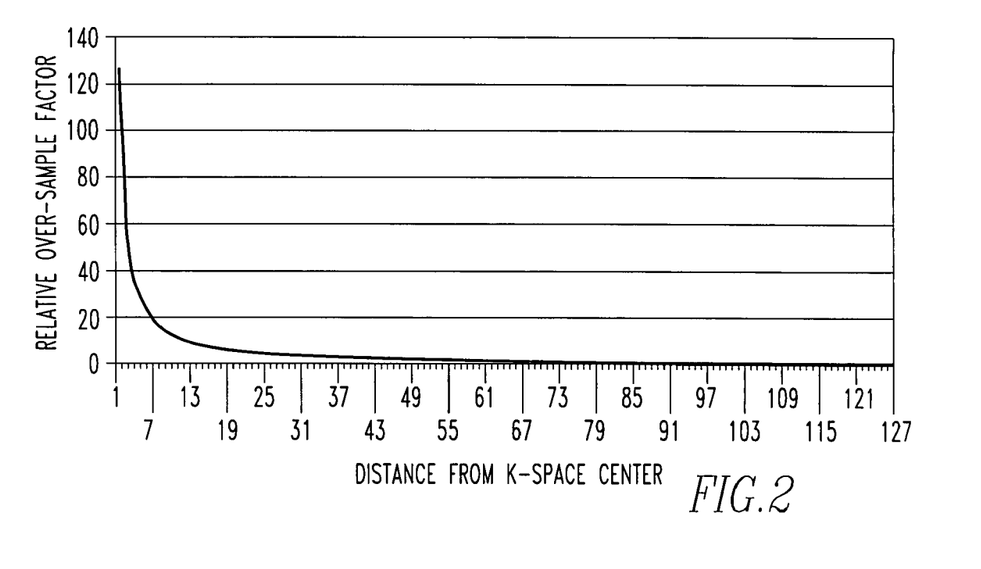
FIG. 2 is an illustration of the form of the relative density of k-space coverage for a radial scan and a parallel line scan.

FIG. 1A shows the k-space lines arranged in a parallel manner that is typical of an MRI acquisition. In MRI, the lines are typically acquired parallel to one major axis, and are evenly spaced through the matrix. The spacing of k-space lines is given by the Nyquist criteria, such that the spacing $\Delta K$, is given by Field of View=$2 \times n/\Delta K$. FIG. 1B corresponds to an acquisition of projective data, where each projection is represented by a separate line passing through the center of k-space, i.e. radial data. The key feature of the radial plot is that the concentration of k-space lines is highest at the center and gets progressively less towards the periphery of k-space.

To satisfy the Nyquist criteria in the radial case requires that there are at least twice as many k-space lines as present in the corresponding parallel case.

FIG. 2 is an illustration of the form of the relative density of k-space coverage for a radial scan and a parallel line scan. The vertical axis plots the density of k-space sampling, and shows that the data are relatively over sampled by up to a factor of greater than 60 in this case, but that the relative density falls to about 0.5 in the outer regions of k-space, the horizontal axis plots the radius from the center of k-space. The exact shape and amplitude of the relative sampling pattern varies as a function of the over sample factor used for the radial scan, with an over sample value of 2 or higher being typical.

Previously, in dynamic MRI applications, it was noted that parallel lines of k-space data can be sparsely sampled and subsequently temporally interpolated to fill in the missing data. Under the condition that a certain principle is followed, this method of sparse sampling and data interpolation represents the temporally changing data without introducing temporal blur or spatial artifact above levels comparable to the noise that is inherent in the MRI data, while reducing the scan time by a factor of 4 or higher. The principle guiding the sparse sampling and interpolation process is that data nearest the center of k-space are sampled at the highest temporal rate, while data progressively closer to the periphery of k-space are sampled at progressively lower temporal rates. However, direct application of this to a time resolved radial data set is not possible without introducing distortion to the data. Consider the case where each radial line is sparsely sampled with a temporal skip factor of 4, FIG. 3. In this case each k-space point is separated by 3 missing points, irrespective of the distance from the center of k-space. Applying temporal interpolation to his data would lead to too low a temporal update rate near the center of k-space, leading directly to temporal blur of the time series.

Figure 3:
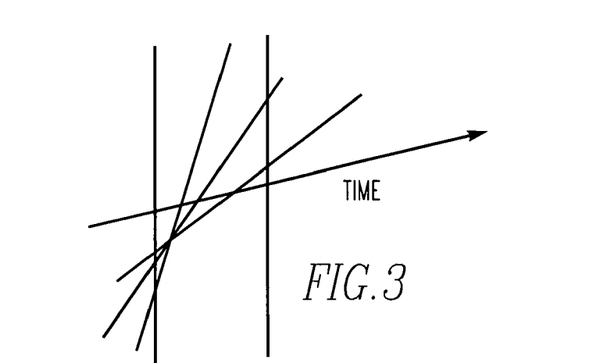
FIG. 3 is an illustration of how a series of radial lines are acquired over time.

FIG. 3 is an illustration of how a series of radial lines are acquired over time. In this illustration, the first radial line is re-sampled only after three separate radial lines are sampled. In this manner, each radial line will be sampled at every fourth time point.

It is instructive to note that the central region of k-space corresponds to low-resolution features in the final image that largely contribute to broad contrast features, which typically change in a rapid manner. Conversely, the outer regions of k-space correspond to fine detail in the final image, but provide very little contrast information, and these regions vary in a relatively slow temporal manner.

The exact manner in which the STAR approach can be used to achieve rapid imaging is to some extent coupled to the manner in which radial data are acquired. In MD-CT scanning, for instance, the scanner detector rapidly rotates around the body and it is more feasible to acquire radial data in a sparse manner (to be illustrated below). In this arrangement, the radiation dose (which is typically a limiting factor of MD-CT) can be reduced. Alternatively, for gated-SPECT imaging, the scanner detector can only move relatively slowly, and radiation dose is not dependent on the scan time. In this case, it is advantageous to apply STAR to increase spatial and temporal resolution (to be illustrated below) since these are typically limiting factors of gated-SPECT data sets.

Application Example Most Suitable for MD-CT

Figure 4:
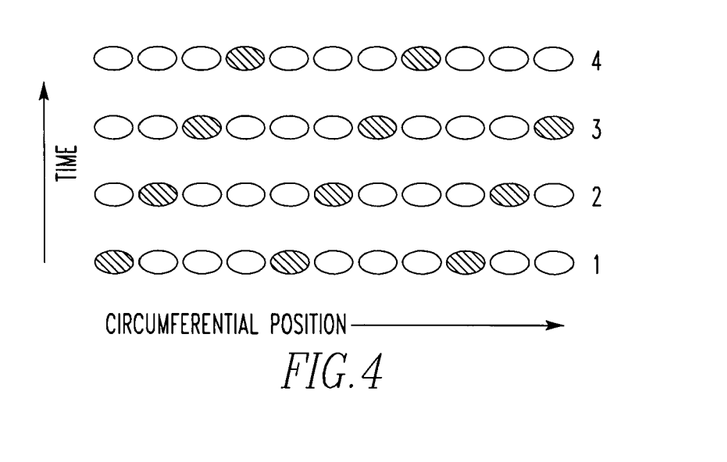
FIG. 4 shows an application of STAR to a modality such as MD-CT.

To illustrate the basic principle of STAR that is applicable for modalities such as MD-CT, consider that the conventional radial sampling scheme employs an over-sample factor of 2. Taking this as the reference data set, implement STAR by sampling only every 4th radial lines of k-space at each time point, i.e. the net acquisition time is reduced by a factor of 4. When viewed as a time-radial sampling plot, the sampled points and skipped data are distributed as shown in FIG. 4. In this representation, the position of the sampled points and the skipped points are known for each radial position. From the principles established in prior dynamic MRI data, it is possible to interpolate the sampled data to generate data at points not sampled, such that the generated data are close in value to the true data (within limits typical of noise levels), providing that data are adequately sampled along the interpolation direction. In the STAR invention, the time vs. radial position data are treated separately depending on whether the radial position corresponds to a k-space region that is relatively over-sampled or under-sampled compared to the comparable parallel line scan. In this example, k-space is relatively over-sampled for points up to one quarter of the radius from the center, and from the center to this boundary, data are interpolated only along the circumferential direction. Conversely, and for data extending from this boundary to the periphery of k-space, data are sampled at a rate less than the critical Nyquist limit and are interpolated only along the temporal axis. In this case, the separation along the temporal axis of identical sample positions is 4 time points. By this general strategy, all of the skipped points are filled in. Importantly, by interpolating using this two tiered scheme, data conform or approximate to the principles established for dynamic MRI data, i.e. within the over sampled region, no temporal interpolation is applied, while points outside of the critical Nyquist circle are filled in by applying only temporal interpolation.

FIG. 4 shows an application of STAR to a modality such as MD-CT, illustrating the temporal and circumferential distribution of sparsely sampled views at one particular radial position, shown for four concessive time points (1-4). The view shown here for one particular radial position is that radial lines are directed into and out of the plane of the page (like spokes of a bicycle wheel pointing towards the viewer). The vertical axis of the figure represents progression around the circumference, and the horizontal axis represent progression of time. The dark shaded circles represent data that are acquired. Open shaded circles represent positions where radial lines are conventionally acquired but that are not sampled in this particular sparse sample scheme.

Application Example Most Suitable for Gated-SPECT

To illustrate the basic principle of STAR that is most applicable for modalities such as gated-SPECT, consider the scan being performed to increase scan resolution and improve temporal resolution. In example shown in FIG. 5, the number of radial projections are doubled and the temporal resolution within the cardiac cycle is also doubled. Conventionally, implementing both of these measures would quadruple the scan time and result in a reduction in the SNR by a factor of about 3. However, when STAR is used, it is arranged for the scanner to dwell at each radial position for a fraction (in this case 50%) of the conventional time (conventionally, the scanner dwells at each position until a certain number of counts are obtained, such as 5,000,000), and to bin the data temporally into double the number of time slots. In this way, high spatial and temporal resolution data will be acquired, but will typically not be of diagnostic value to the excessive noise contamination.

Figure 5:
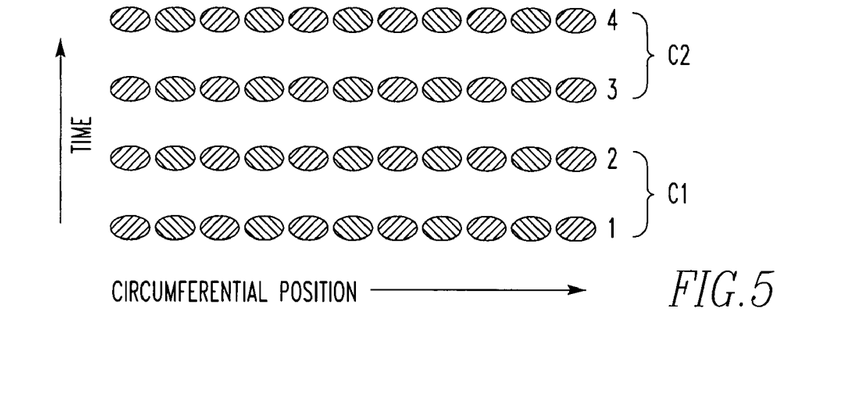
FIG. 5 shows an application of STAR to a modality such as gated-SPECT.

FIG. 5 shows an application of STAR to a modality such as gated-SPECT illustrating the temporal and circumferential distribution of highly sampled views at one particular radial position, shown for four concessive time points (1-4). The view shown here for one particular radial position is that radial lines are directed into and out of the plane of the page (like spokes of a bicycle wheel pointing towards the viewer). The vertical axis of the figure represents progression around the circumference, and the horizontal axis represent progression of time. The dark shaded circles represent data that would have been conventionally acquired, and the light shaded circles represent the additional radial data that are acquired for STAR. The designation C1 and C2 indicate that conventionally data would be acquired over a temporal duration of twice the duration of that used for STAR in this example. In this case, there are double the number of time points available in the STAR acquisition.

When the fully resolved gated-SPECT data set has been acquired it is subjected to data processing using the STAR approach to improve the signal to noise ratio. In this data set, the boundary of the over sampled region of k-space is identified and within this region (i.e. towards the center of k-space) the fully sampled circumferential data, at each radial position, are filtered along the circumferential direction by applying a low pass filter. The pass width of the filter is determined by the relative density of k-space sampling, e.g. for the case where the sampling density is twice the Nyquist limit, then the band-pass filter would allow through only half of the frequency response data, FIG. 6. Conversely, for radial data at a position outside of the over-sampled region, the data will be low pass filtered along the temporal direction, FIG. 7. The band-pass width of the low-pass filter is established according to the position along the radial distance from the center of k-space starting with low pass filter width being equal to the full bandwidth at the Nyquist boundary, and progressively reducing towards the periphery of k-space. The lower limit of the band-pass filter could be set to allow through a fraction, such as $\frac{1}{8}^{th}$ of the full temporal bandwidth. By applying bandwidth filtering in the manner prescribed by STAR, noise is removed, while allowing the essential features of the data to remain, thus improving the SNR of the gated-SPECT data set.

Figure 6:
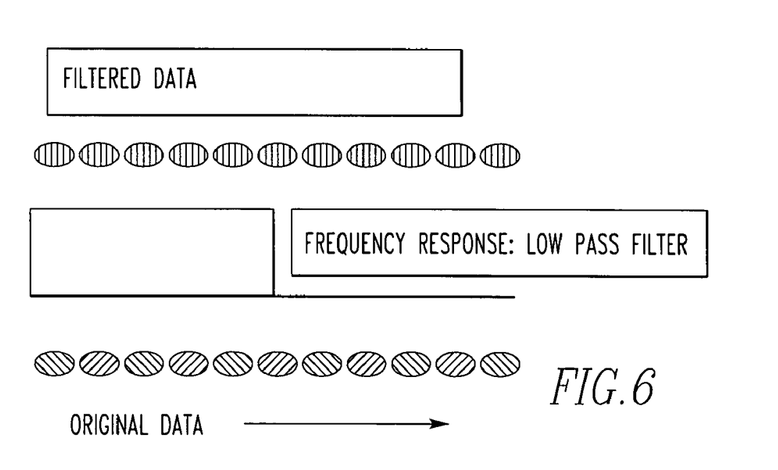
FIG. 6 shows the low pass filtering of the circumferential data in STAR.

FIG. 6 shows the low pass filtering of the circumferential data in STAR. In this case, the original circumferentially sampled points are converted to the frequency domain by performing a Fourier transform. In this form, the data are subjected to a low pass filter. The filtered data are converted back to projection data, but with reduced noise.

Figure 7:
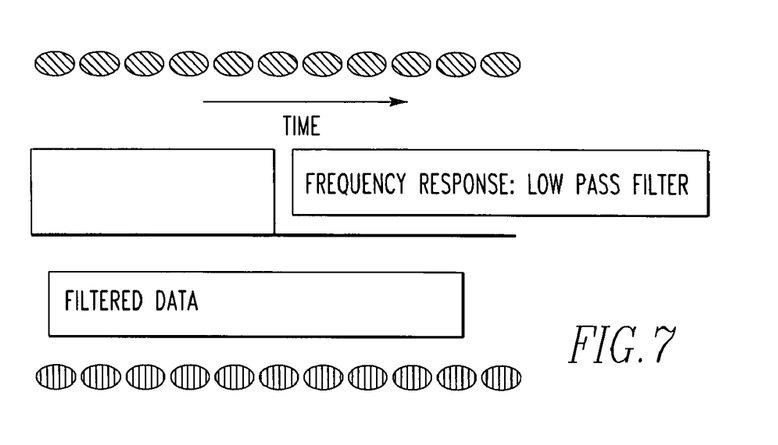
FIG. 7 shows the low pass filtering of the temporal data in STAR.

FIG. 7 shows the low pass filtering of the temporal data in STAR. In this case, the original temporally sampled points are converted to the frequency domain by performing a Fourier transform. In this form, the data are subjected to a low pass filter. The filtered data are converted back to projection data, but with reduced noise.

Figure 8:
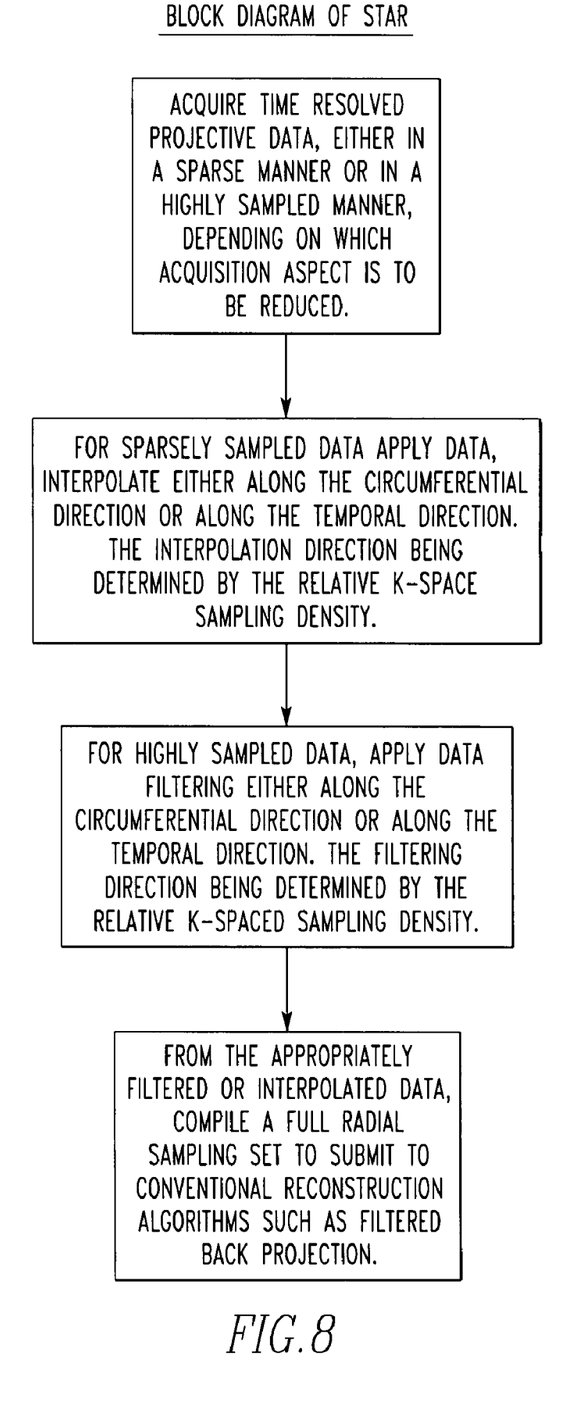
FIG. 8 is a block diagram of STAR.

A block diagram of the essential features of STAR is shown in FIG. 8.

The invention has a dramatic impact on several technologies, including magnetic resonance imaging (MRI), multiple detector computed tomography (MD-CT), and gated radionuclide single photon computed tomography (gated-SPECT) nuclear imaging. The particular advantage for MD-CT approaches is that radiation exposure (which is a limiting factor) would be reduced by about 75% compared to a conventional scan. The advantage to gated-SPECT imaging would be that higher spatial and temporal resolution data could be obtained in a standard scan time (since radiation exposure is not as problematic, but image resolution is currently a limiting factor).

Differences and Advantages of this Technology Over Other Technology or Prior Art:

No other approach combines the features of STAR in that interpolation or filtering is applied circumferentially or temporally based on the density of sampling of k-space. In the signal processing literature, there are approaches that will reconstruct projective data with improved SNR characteristics. Typically, these approaches are applicable to each individual time frame, and could reduce the scan time. However, the STAR approach does not preclude these reconstruction approaches being used to achieve further reductions in scan time, since STAR specifically takes into account the spatial and temporal nature of the data.

Figure 9:
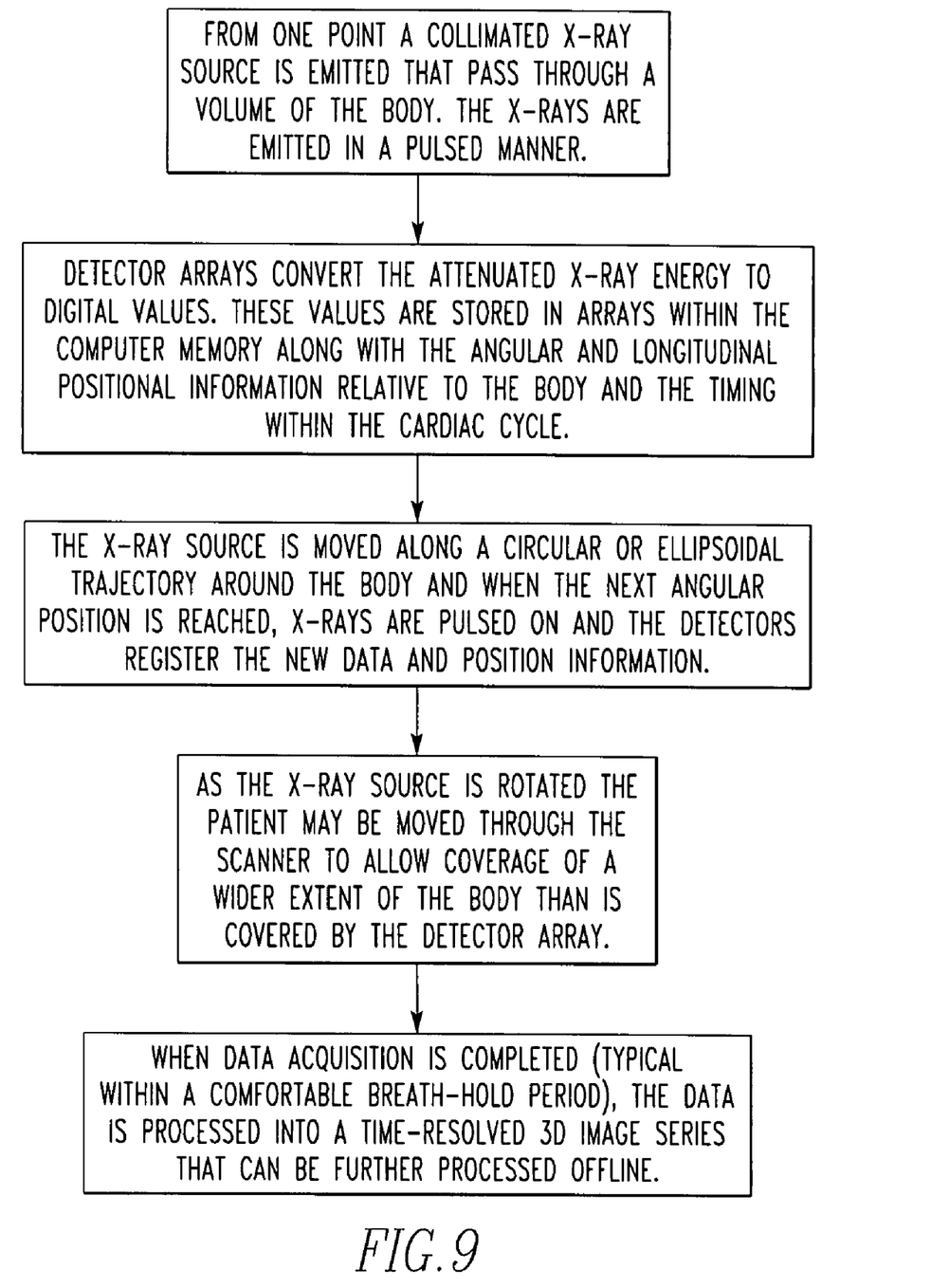
FIG. 9 is a block diagram of CT hardware for computed tomography in regard to STAR.

Description of CT Hardware that Supports the Invention:

The hardware that accomplishes CT imaging has several variants with four distinct "generations" of technology are recognized. The variations are largely concerned with whether the detectors move relative to the x-ray source 22, how-many detectors are used, and whether the x-ray source 22 moves around the body in a continuous circle or partial circular path. These variants do not affect the essential features of the STAR invention. The essential features of the CT system are noted in the block diagram and are: an x-ray source 22 that is applied in a pulsed mode to irradiate the body, an array of detectors where the signal is digitized and stored in a memory 18 along with information concerning the relative angle, longitudinal position and timing within the cardiac cycle. A series of projection data sets are obtained in this way that relate to several slices and times within the cardiac cycle. For one cardiac phase time as it relates to an individual slice, the projection data are acquired at a series of angular positions around the body. To obtain increased resolution, an increased number of projections are required, with the variable that increases being the number of projections per unit angle.

Figure 10:
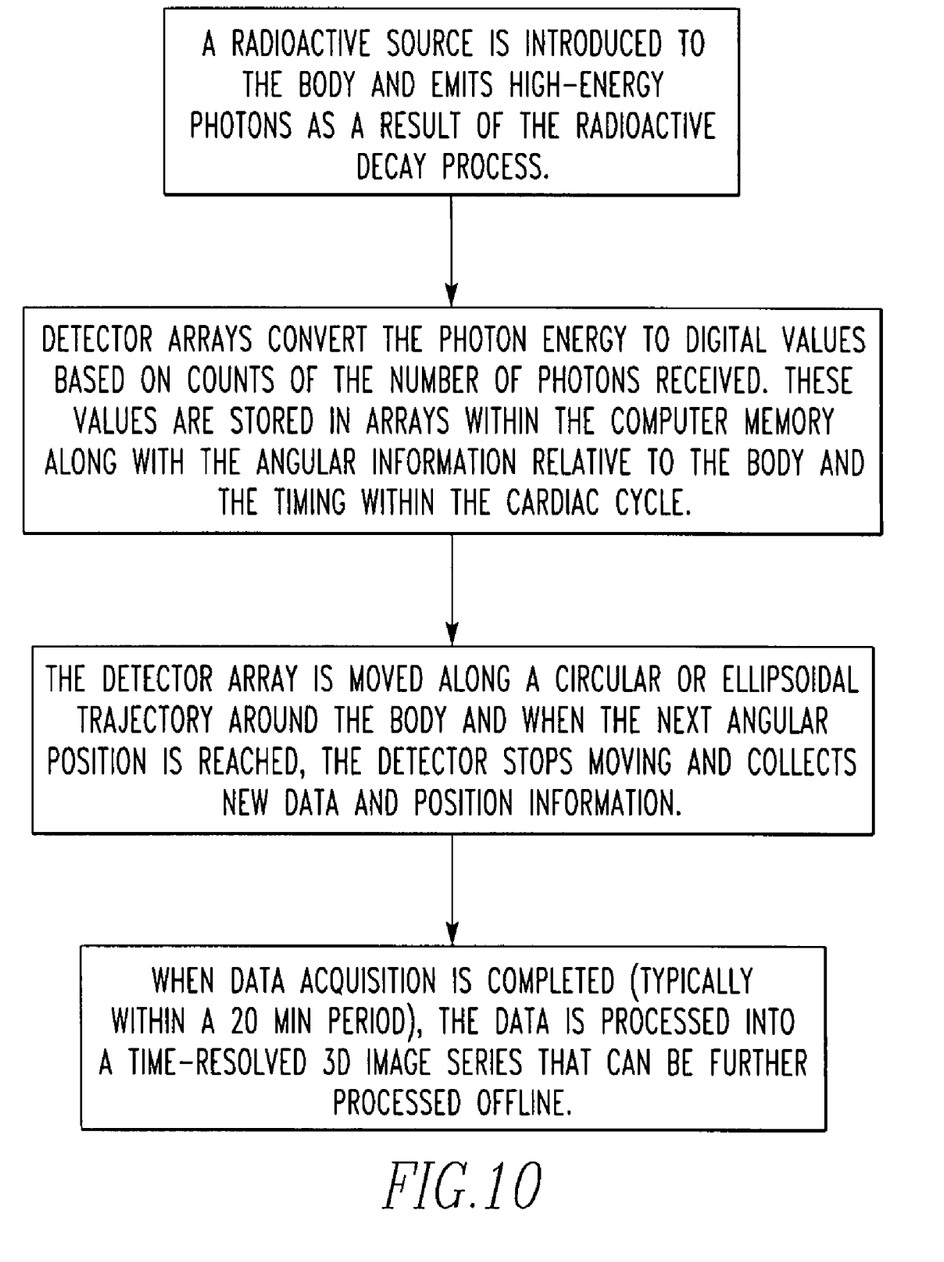
FIG. 10 is block diagram of gated SPECT hardware in regard to STAR.

Description of Gated SPECT Hardware that Supports the Invention:

The essential features of the gated SPECT system are noted in the block diagram and are: an array of detectors that convert high-energy photons into an electrical signal. The photons are emitted from a radioactive source 28 within the body. The signal from each detector is digitized and stored in a memory 18 along with information concerning the relative angle and timing within the cardiac cycle. A series of projection data sets are obtained by moving the detector array 24 to a new location following an ellipsoidal path around the body. In this way data relating to several slices and times within the cardiac cycle are obtained. To obtain increased resolution, an increased number of projections are required, with the variable that increases being the number of projections per unit angle.

Figure 11:
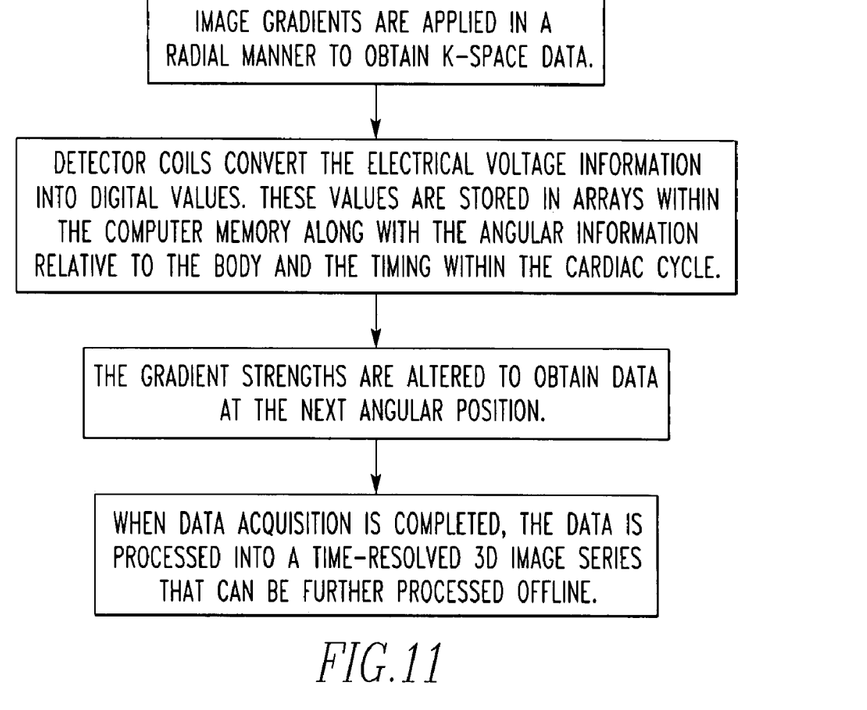
FIG. 11 is a block diagram of MRI hardware in regard to STAR.

Description of MRI Hardware that Supports the Invention:

The essential features of the MRI system are noted in the block diagram and are: a series of gradients are applied to acquired k-space lines in radial manner. The signal from each receiver coil element is digitized and stored in a memory 18 along with information concerning the relative angle and timing within the cardiac cycle. A series of projection data sets are obtained by altering the relative gradient strengths. In this way data relating to several slices and times within the cardiac cycle are obtained. To obtain increased resolution, an increased number of projections are required, with the variable that increases being the number of projections per unit angle.

Nyquist Sampling Criteria

The density with which k-space has to be sampled without introducing signal aliasing is governed by the Nyquist sampling criteria. In relationship to radially sampled lines, separation of one line from another varies with distance from the center of k-space. In this situation, the widest separation of k-space lines occurs at the periphery, and the Nyquist sample criteria is given by:

$$\text{Field of View} = 2 \times n/\Delta K$$

Figure 12:
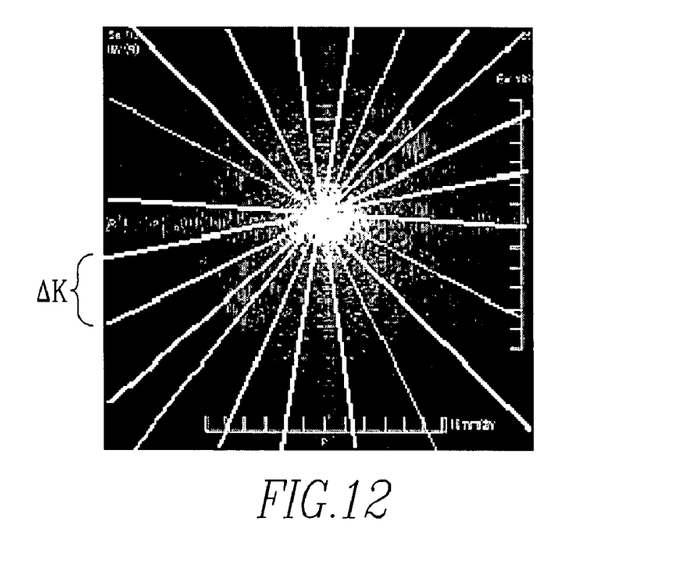
FIG. 12 is a schematic of the k-space sampling pattern for radial lines.

A schematic of the k-space sampling scheme relative to ΔK is shown in FIG. 12. Under conditions that the equation relating field of view to ΔK is satisfied, the k-space matrix is said to be fully sampled. If the separation ΔK is less than indicated by the field of view, then k-space is regarded as highly sampled, and under conditions that the separation ΔK is greater than indicated by the formula relating it to the field of view, then k-space is said to be sparsely sampled.

Conversion of Projective Data to Radial Data

In MRI, it is natural to consider the source data in terms of k-space, which directly relates to the image space by a 2D Fourier transform (in the case of 2D data). However, in modalities such as gated-SPECT and CT, it is more natural to consider the data as a series of projections. This projective data is typically arranged in a signal space termed Radon space. For the STAR invention, it is necessary to convert the Radon space data corresponding to one slice into the k-space format, arranging it in a 3D matrix, with two k-space dimensions and one time dimension. To convert each individual projective data set into k-space, the data are subjected to a Fourier transform. The projective data are a projection of some energy function through a 2D slice of the patient and consists of a 1D profile. The corresponding Fourier transformed data is also a 1D profile. In the Fourier transform format, the data is inserted into the 3D k-space matrix such that the center of the transform data is positioned at the center of k-space (for a given time position along the 3D data set) and that the angle of the transform data corresponds directly to the angle of the original projection data. In this way, a series of projective data are arranged to form a k-space data set that is based on a radial distribution spread over time.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. An apparatus for forming an image of a body of a patient comprising:
    an energy source which emits energy that passes through the body or which causes the body to emit energy;
    at least one detector element which receives the energy which has passed through, or originated within the body;
    a computer with a memory in communication with the detector element which stores in the memory angular and timing information relative to the body regarding the energy; and
    means for obtaining additional angular and timing information relative to the body regarding the information including the computer-generated steps from a computable readable medium of:
    acquiring time resolved projective data, either in a sparse manner or in a highly sampled manner, depending on which acquisition aspect of the patient is to be reduced;
    interpolating either along a circumferential direction or along a temporal direction of the sparsely sampled data, the interpolation direction being determined by a relative k-space sampling density;
    applying data filtering either along the circumferential direction or along the temporal direction for highly sampled data, the filtering direction being determined by the relative k-space sampling density;
    compiling a full radial sampling set from the filtered or interpolated data; and
    submitting the sampling set for reconstruction.

2. An apparatus as described in claim 1 wherein the source is a collimated x-ray source.

3. An apparatus as described in claim 2 wherein the detector element includes a detector array.

4. An apparatus as described in claim 3 wherein the obtaining means includes a motor or electrical control which moves the x-ray source.

5. An apparatus as described in claim 1 wherein the energy source includes a radioactive source which is adapted to be introduced to the body and which emits high-energy photons as a result of radioactive decay.

6. An apparatus as described in claim 5 wherein the detector element includes a detector array.

7. An apparatus as described in claim 6 wherein the obtaining means includes a motor which moves the detector array along a circular or an ellipsoidal trajectory around the body and when a next angular position is reached, a motor stops moving the detector array and the detector array collects new data and position information.

8. An apparatus as described in claim 1 wherein the energy source produces imaging gradients that are applied in a radial manner to obtain k-space data.

9. An apparatus as described in claim 8 wherein the detector element includes a detector coil and electronics which converts electrical voltage information into digital values.

10. An apparatus as described in claim 9 wherein the obtaining means includes altering the imaging gradients strengths to obtain data at a next angular position.

11. A method for forming an image of a patient comprising the steps of:
    acquiring time resolved projective data, either in a sparse manner or in a highly sampled manner, depending on which acquisition aspect of the patient is to be reduced;
    interpolating either along a circumferential direction or along a temporal direction sparsely sampled data, the interpolation direction being determined by a relative k-space sampling density;
    applying data filtering either along the circumferential direction or along the temporal direction for highly sampled data, a filtering direction being determined by the relative k-space sampling density;
    compiling a full radial sampling set from the filtered or interpolated data; and
    submitting the sampling set for reconstruction.

12. A method as described in claim 11 including the step of reconstructing the sampling set to form the image.

13. A method as described in claim 12 including the step of emitting energy that passes through the body.

14. A method as described in claim 13 including the step of receiving the energy which has pass through the body with at least one detector element.

15. A method as described in claim 14 including the step of storing in a memory of a computer in communication with the detector element angular and timing information relative to the body regarding the energy.

16. A method as described in claim 15 including the step of obtaining additional angular and timing information relative to the body regarding the information.

* * * * *